United States Patent [19]

Larkin et al.

[11] Patent Number: 5,071,404

[45] Date of Patent: Dec. 10, 1991

[54] INJECTION SITE

[75] Inventors: Mark E. Larkin, Lindenhurst; Richard W. Grabenkort, Barrington, both of Ill.

[73] Assignee: Abbott Laboratories, Abbott Park, Ill.

[21] Appl. No.: 388,266

[22] Filed: Aug. 1, 1989

[51] Int. Cl.$^5$ .............................................. A61M 5/00
[52] U.S. Cl. ...................................... 604/86; 604/244; 215/247
[58] Field of Search ...................... 604/82, 83, 86, 88, 604/167, 244, 256, 284, 415; 215/247

[56] References Cited

U.S. PATENT DOCUMENTS

| | | | |
|---|---|---|---|
| 3,757,981 | 9/1973 | Harris, Sr. et al. | 215/247 |
| 4,219,912 | 9/1980 | Adams | 604/86 |
| 4,294,249 | 10/1981 | Sheehan et al. | 604/86 |
| 4,405,316 | 9/1983 | Mittleman | 604/86 |
| 4,412,573 | 11/1983 | Zdeb | 604/415 |
| 4,416,661 | 11/1983 | Norman et al. | 215/247 |
| 4,596,557 | 6/1986 | Pexa | 604/86 |
| 4,874,369 | 10/1989 | Kulle et al. | 604/86 |

FOREIGN PATENT DOCUMENTS 2805354 9/1978 Fed. Rep. of Germany ........ 604/86

*Primary Examiner*—Stephen C. Pellegrino
*Assistant Examiner*—Ralph A. Lewis
*Attorney, Agent, or Firm*—A. Nicholas Trausch

[57] ABSTRACT

An injection site for the infusion of a medicament into a flow path for a parenteral fluid and, more particularly, an injection site which is essentially self-priming and air-occluding and which is of extremely simple construction and easily assembled. Furthermore, the invention is also directed to an injection site of the type described herein which is especially adapted for use as an injection port of a Y-connector utilized for an intravenous administration set. The device incorporates a self-sealing puncturable member of resilient material, such as rubber, which member is of a substantially spheroid configuration, the tubular segment so as to be in close proximity to the and which is swage-molded into a receiving housing in the tubular segment so as to be in close proximity to the inlet tubing for the flow path of the parenteral fluid. This, in effect, will largely eliminate the formation of any potential spaces in which air may be entrapped at the injection site while, concurrently, the generally spherical configuration of the puncturable member, particularly the curvilinear surface which is contiguous with the flow path for the parenteral fluid, will cause any minute quantities of introduced air, if at all present, to be conducted out of the inlet for the parenteral fluid so as to essentially render the device self-priming.

4 Claims, 2 Drawing Sheets

INJECTION SITE

BACKGROUND OF THE INVENTION

1. Field of the Invention

The present invention relates to an injection site for the infusion of a medicament into a flow path for a parenteral fluid and, more particularly, relates to an injection site which is essentially self-priming and air-occluding and which is of extremely simple construction and easily assembled. Furthermore, the invention is also directed to an injection site of the type described herein which is especially adapted for use as an injection port of a Y-connector utilized for an intravenous administration set.

As is widely known, medicaments are frequently administered as a supplement through the employment of various devices employed in conjunction with intravenous administration sets, wherein such supplementary medicaments while in a liquid condition are usually introduced through the intermediary of a hypodermic needle which is temporarily inserted through a resealable puncturable closure provided at an injection site so as to infuse the medicament into a parenteral fluid for delivery therewith to a patient.

In general, such parenteral liquids and supplemental medicaments are intravenously administered to the patient in that the Y-connector for the intravenous administration set incorporates a plurality of communicating tubular arms, in which one arm forming a first inlet branch is connected to a source for the supplying of the parenteral fluid, the latter being continually dispensed into the tubular arm in an air-occluding flow so as to be conducted through a second tubular arm of the Y-connector discharging into a tubular conduit arrangement which may be connected to a catheter inserted into a vein of the patient. When, upon occasion, it becomes necessary to administer medications to a patient who may be in a comatose state or otherwise unable to receive such medication through oral administration, it becomes expedient to introduce any such medicament into the parenteral fluid while in the form of a fluid, for which purpose a third arm of the Y-connector, which intersects and communicates with the other arms incorporates a resealable and puncturable member, which member is generally constituted from a resilient and self-sealing, puncturable material, for example, such as rubber, through which a hypodermic needle or syringe may be temporarily inserted in order to inject a desired quantity of the medicament into the parenteral fluid flowing through the Y-connector, and thereafter withdrawn to permit the member closure to reseal itself.

A major problem frequently encountered in conjunction with injection sites of this type resides in that the Y-connector structures incorporating such injection sites which are presently in widespread use tend towards formation of air bubbles or pockets at the injection sites during the injecting of the medicament, and whereby such air must be removed in order to prevent the conveyance of potentially life-threatening entrapped air to the patient while entrained in the parenteral fluid. This frequently entails having to expend considerable periods of time in priming the Y-connector in attempting to remove any entrapped air; in essence, by tapping and/or orientation thereof in various positions by a nurse or other medical personnel so as to cause entrapped air to flow back and be discharged from the inlet for the parenteral fluid.

Moreover, various structures which are employed in the formation of such injection sites are either relatively complicated and expensive in construction and/or difficult to properly install in the Y-connector. Consequently, various attempts have been made in the technology, which are intended to simplify the structures and designs of such types of injection sites, while concurrently inhibiting the formation of potential air pockets or entrapped air bubbles which would necessitate the expenditure of considerable time and effort in having to prime the Y-connector to eliminate any air entrapped therein.

2. Discussion of the Prior Art

Sheehan, et al. U.S. Pat. No. 4,294,249 discloses a swage-molded injection site which, in one specific application thereof, may be employed in a Y-connector for an intravenous administration set, wherein the injection site includes a tubing segment constituted from a rigid and moldable plastic material. A self-sealing puncturable cylindrical member of a resilient material, such as rubber, is inserted into a housing portion in the tubing segment, with an upper edge thereof then being swaged over the periphery of the puncturable member so to cause the latter to be sealingly fixed in position within the housing. Although this particular design for an injection site allows for a simple manufacture thereof with only few components while securely sealing the puncturable member in fixed engagement within the tubular housing provided for this purpose in the Y-connector, the particular arrangement thereof allows for the entrapment of quantities of air in the interior passageway thereof communicating with the flow path for a parenteral liquid. Consequently, in order to eliminate the presence of entrapped air from the device, considerable effort must be expended by medical personnel in order to be able to remove such entrapped air to prime the device for operation with the intravenous supply of the parenteral fluid and medicament to the patient.

Efforts to eliminate such pockets of entrapped air from an injection site have been made in formulating the design of an injection port for an intravenous tube, as disclosed in Pexa U.S. Pat. No. 4,596,557. In that instance, the injection site of an intravenous tube incorporates a resilient member of a puncturable self-sealing material, such as rubber or the like, through which a hypodermic needle may be inserted for the infusion of a medicament into a flow of a parenteral fluid being intravenously administered to a patient. In the disclosed construction, the puncturable resilient member is basically a cylindrical plug which includes a tapered or obliquely angled internal end surface which terminates substantially coextensive with the flow path of the parenteral fluid being introduced therein, to thereby preclude the formation of air pockets and to resultingly reduce any necessary priming time for the device. However, the specific structure of the puncturable resilient member with an oblique internal end surface necessitates that during the installation thereof this end surface be precisely oriented and obliqued relative to the flow passageway for the parenteral fluid, and that it be anchored or adhered secured against any displacement to the wall structure of the supporting intravenous tube, inasmuch as any rotation of the resilient member subsequent to its installation would misalign the inner end surface thereof and produce a "dead space" forming a pocket of entrapped air which may be difficult to dislodge and eliminate. Moreover, this construction necessitates the utilization of additional components for securing the resilient member to the surface of its supporting tubing, which renders the entire construction cumbersome and expensive.

Further injection sites of the type considered herein are disclosed in Becker, Jr. U.S. Pat. No. 4,121,585; Zeddies, et al U.S. Pat. No. 4,005,710; Spademan U.S. Pat. No. 3,853,127; Muto U.S. Pat. No. 4,475,548; Norman, et al. U.S. Pat. No. 4,416,661; Turner U.S. Pat. No. 4,289,129; and Vaillancourt U.S. Pat. No. 4,585,435. However, none of these disclose injection sites which are as simple in construction as the inventive injection site which would readily occlude the formation of air pockets or bubbles to thereby practically eliminate or at least substantially reduce the necessity for having to prime the intravenous administration device.

SUMMARY OF THE INVENTION

Accordingly, in order to overcome the limitations and drawbacks which are encountered in prior art injection sites, the present invention has the object of contemplating the provision of a self-priming and air-occluding injection site employed for the infusion of a medicament into a flow path for a parenteral fluid, particularly in connection with but not limited to a Y-connector for use with an intravenous administration set, and in which a tubular arm segment for the introduction of the medicament through the intermediary of a hypodermic needle, incorporates a self-sealing puncturable member of resilient material, such as rubber, which member is of a substantially spheroid configuration, and which is swage-molded into a receiving housing in the tubular segment so as to be in close proximity to the inlet tubing for the flow path of the parenteral fluid. This, in effect, will largely eliminate the formation of any potential spaces in which air may be entrapped at the injection site while, concurrently, the generally spherical configuration of the puncturable member, particularly the curvilinear surface which is contiguous with the flow path for the parenteral fluid, will cause any minute quantities of introduced air, if at all present, to be conducted out of the inlet for the parenteral fluid so as to essentially render the device self-priming. This will considerably reduce, and possibly even eliminate, the time and effort which must be expended by personnel in priming the device for intravenously administering medicament-containing parenteral fluid to a patient, and because of the simple swage-molded construction of the injection site, to extensively reduce the overall costs and installation requirements for the device.

Accordingly, it is a primary object of the present invention to provide an injection site for the infusion of a medicament into a flow path for a parenteral fluid which is of simple construction and is essentially of an air-occluding self-priming nature.

Another object of the present invention is to provide an injection site of the type described herein which is especially adapted for utilization in a Y-connector for an intravenous administration set, and which is self-priming and occludes the formation of air pockets while being extremely simple in construction.

BRIEF DESCRIPTION OF THE DRAWINGS

The foregoing and other advantages and features of the invention may now be more readily ascertained from the following detailed description of a preferred embodiment of an injection site, taken in conjunction with the accompanying drawings; in which.

DETAILED DESCRIPTION

Figure 2:
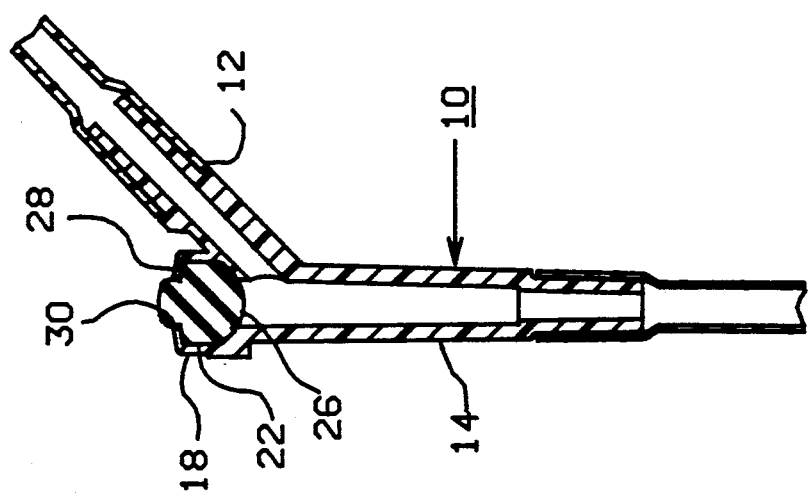
FIG. 2 illustrates the puncturable member in a view similar to FIG. 1 as having been installed and permanently mounted in the Y-connector through swaging of the latter; being
Figure 1:
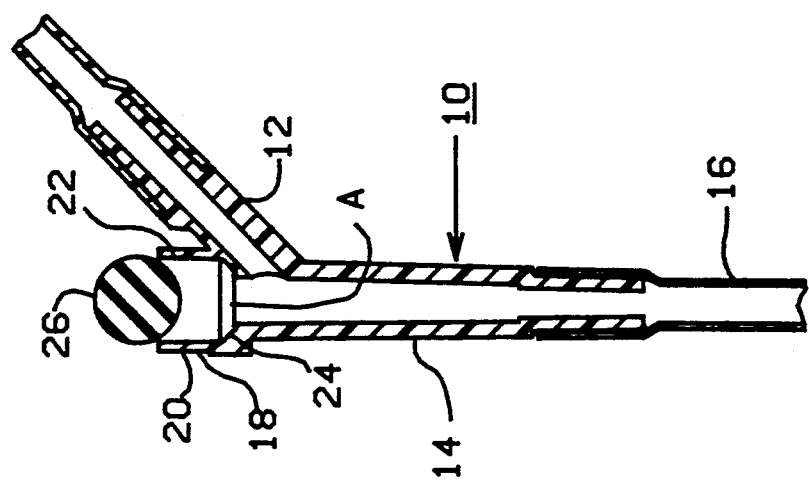
FIG. 1 illustrates a generally diagrammatic longitudinal sectional view through a Y-connector for an intravenous administration set during a stage of having the self-sealable puncturable member of the injection site being installed therein.

Referring now in detail to the drawings, and particularly to FIGS. 1 and 2, there is illustrated a Y-connector 10 of the type which is usually employed in connection with intravenous administration sets (not shown). The Y-connector 10, which may be constituted from a suitable plastic material such as a styrene-acrylonitrile or acrylonitrile-butadiene-styrene among other similar materials, includes a basically three-arm structure; in essence, a first tubular arm 12 which serves as an inlet conduit or flow passageway for the introduction of a parenteral fluid for intravenous administrations to a patient through a suitable catheter, a main or outlet tubing 14, which may have its discharge end connected to a further flexible tubing 16 leading to a catheter or intravenous needle, and a third arm portion 18 which intersects with the arm portions 12 and 14 at generally the location A to form a Y-shaped configuration.

The arm portion 18 which incorporates the novel injection site pursuant to the invention, and which is short in comparison with the other two arms 12 and 14, includes a generally cylindrical housing portion 20, having cylindrical inner sidewalls 22, and a lower generally curvilinear or spherical ledge 24 communicating through an opening with the flow passageways of tubular arms 12 and 14 at location A.

A resealable, and puncturable resilient member 26 of ball-shaped or spherical configuration, which is preferably constituted from rubber or similar material, is adapted to be inserted into the housing 20, as shown in FIG. 1, with the spherical member 26 preferably having a diameter which is slightly larger than the internal diameter or cylindrical dimension 22 of housing 20 so as to be compressed upon insertion therein, and in which the spherical member 26 is pressed downwardly into sealing surface contact against the curvilinear or spherically-curved edge surface 24. Thereafter, the upper end of the housing 18 is either heat-swaged or ultrasonically swaged, as shown in FIG. 2, to form an inwardly extending annular ledge 28 sealingly compressing the upper peripheral portion of the spherical member 26 while permitting a part thereof to sealing extend through a central opening 30 at the swaged outer end of tubular arm portion 18 to allow for access of a suitable hypodermic needle or syringe S for the injection of a medicament. The structure provided for by the inwardly swaged edge 28 forces the spherical member 26 axially downwardly within the housing 22 into sealing surface contact with the ledge 24, while the lower inner surface portion of the spherical member 26 maintains its curvilinear or spherical configuration extending through the opening encompassed by the ledge 24 facing towards the flow passageways defined by tubular arms 12 and 14.

Figure 3:
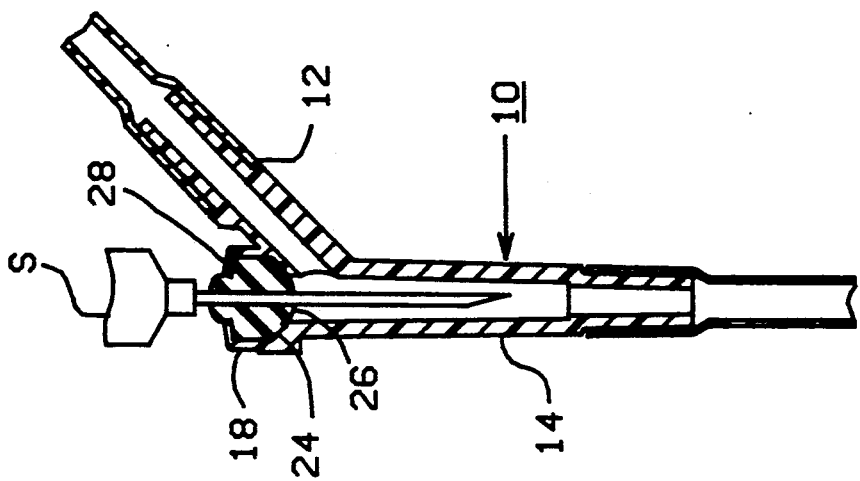
FIG. 3 illustrates the puncturable member pierced by a hypodermic needle for the introduction of a medicament into a flow of a parenteral fluid.

Thus, upon the insertion of hypodermic syringe S through the puncturable, resiliently resealable spherical member 26 for the administration of medicament into the flow of parenteral fluid entering the device through the tubular inlet arm 12, as shown in FIG. 3, the curvature of the spherical member 26 in direct proximity with location A at the intersection of the tubular arm portions 12, 14 and 18, where it projects below the opening in ledge 24, will prevent the formation of any so-called "dead space" which would entrap air. Any introduced air from the hypodermic needle will "roll off" the bottom of spherical member 26 and float upwardly through tubular arm portion 12 to be discharged therethrough. This structural and functional feature will eliminate any need for or largely ameliorate having to prime the device by medical personnel in view of the novel configuration of the spherical surface member 26, and consequently rendering the device essentially self-priming in nature.

Moreover, the employment of the swage-molded structure for the housing 18 in order to retain the spherical resilient member 26 therein eliminates the need for the provision of locking rings or caps, rendering the entire structure simple to manufacture, and in view of the spherical shape of the member 26, the latter may be installed in any orientation which again renders installation and manufacture thereof simple and inexpensive.

Figure 4:
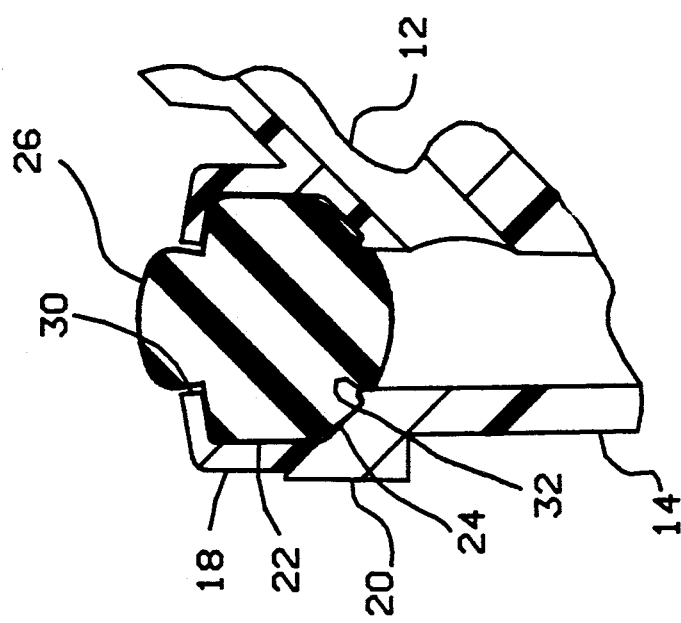
FIG. 4 illustrates, on an enlarged scale, a fragmentary detail of the puncturable member seated on a modified seat in the tubular arm of a Y-connector forming injection site.

A modified embodiment of the injection site is disclosed in FIG. 4, wherein the ledge 24 includes a raised annular bead 32 about the opening seating the lower end of the spherical member 26 thereagainst. The annular bead 32 forms a raised seat which, by pressing into the material of the resilient spherical member 26, reduces the amount of force or surface pressure required for sealing the member 26 against the bottom surface of the ledge 24 of the housing 32.

Figure 6:
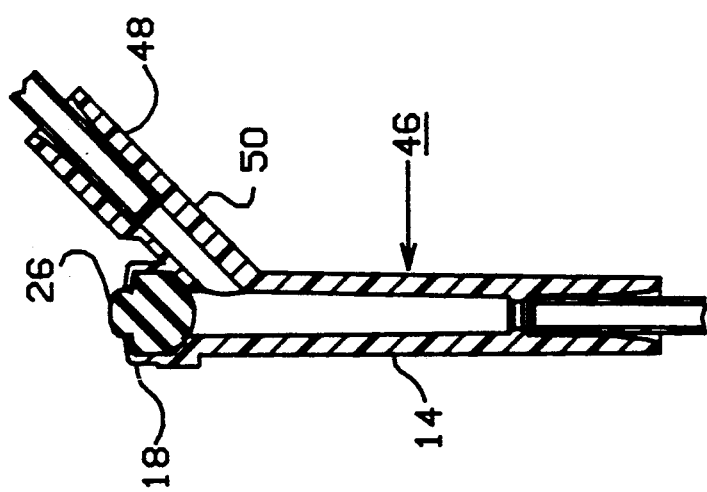
FIGS. 5 and 6 respectively illustrate embodiments of Y-connectors incorporating the inventive puncturable member of the injection site.
Figure 5:
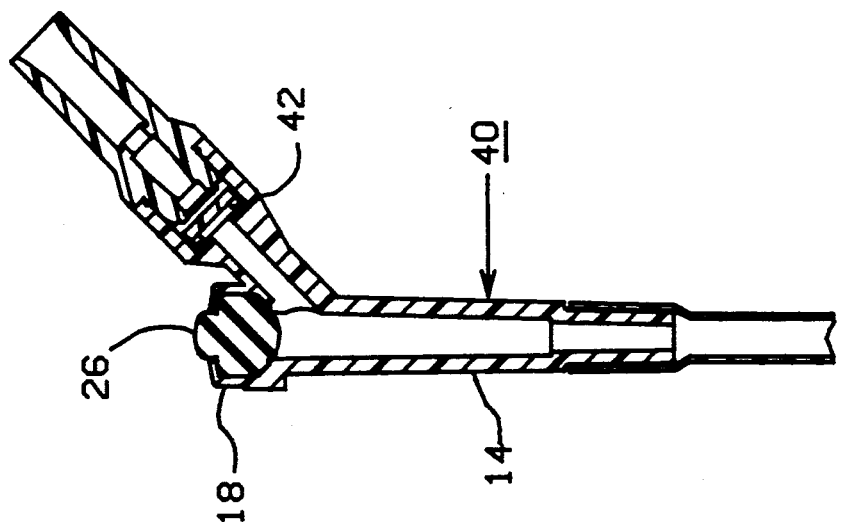

Reverting in particular to the embodiments of the Y-connectors shown in FIGS. 5 and 6 of the drawings, these are primarily analogous in structure to the Y-connector 10 shown in the preceding embodiment; however, in FIG. 5 the Y-connector 40, in the tubular arm 42 for the introduction of the parenteral fluid, incorporates a back check valve; whereas in the embodiment of FIG. 6 the Y-connector 46 incorporates an adhesive or solvent joint 48 in the tubular arm 50 for the introduction of the parenteral fluid. In either instance, the injection site and housing structure 18 containing the spherical member 26 remains identical with the embodiment illustrated in FIGS. 1 through 4 of the drawings.

From the foregoing, it becomes readily apparent to one skilled in the art that the injection site, which is disclosed herein in conjunction with a Y-connector, is extremely simple in construction so as to render the entire device less expensive to manufacture, and easier handled in an intravenous administration set due to its self-priming feature at the injection site.

Furthermore, although the invention relative to the self-priming injection site has been described in connection with a Y-connector, it is readily apparent that the injection site may be readily employed with other types of devices, such as supply bags or containers for administering fluids to a patient and the like.

While there have been shown and described what are considered to be preferred embodiments of the invention, it will of course be understood that various modifications and changes in form or detail could readily be made without departing from the spirit of the invention. It is therefore intended that the invention be not limited to the exact form and detail herein shown and described, nor to anything less than the whole of the invention herein disclosed as hereinafter claimed.

What is claimed is:

1. A self-priming and air-eliminating injection site for the infusion of a medicament into a flow path for a parenteral fluid, comprising in combination:
    (a) a puncturable, self-sealing member of a resilient material, said puncturable member having a generally spheroid configuration; and
    (b) a tubular, plastic housing having a containment space for compressingly confining said puncturable member, said containment space in said housing having an internal sidewall diameter which is smaller than the uncompressed diameter of said puncturable member and a curvilinear surface forming an annular resting ledge for said puncturable member at the bottom end of said space in close proximity to the flow path for said parenteral fluid such that a curvilinear surface of said puncturable member is contiguous with the parenteral fluid flow path, said resting ledge including a raised annular bead extending about a central opening, said bead pressing into the puncturable member in sealing contact therewith, and a swage-molded top edge at the opposite end of said containment space extending over at least a peripheral portion of the upper surface of said puncturable member and imparting a compressive force to said member.

2. An injection site as claimed in claim 1, wherein said injection site is an injection port of a Y-connector for an intravenous administration set, said Y-connector having three interconnecting tubular arms, one said arm being an inlet passageway for the parenteral fluid, a second said arm having said injection site in immediate proximity to the intersection thereof with said first arm, and said third arm joining said first and second arms proximate the curvilinear bottom end of said puncturable member at said intersection to cause said injection site to be self-priming by minimizing the formation of entrapped air at said injection site.

3. An injection site as claimed in claim 1, wherein said tubular plastic housing consists of a material selected from the group of materials consisting of styrene-acrylonitrile and acrylonitrile-butadiene-styrene.

4. An injection site as claimed in claim 1, wherein said puncturable member consists of rubber.

* * * * *